US009241695B2

(12) United States Patent
Peavey et al.

(10) Patent No.: US 9,241,695 B2
(45) Date of Patent: Jan. 26, 2016

(54) PATENT FORAMEN OVALE (PFO) CLOSURE CLIPS

(75) Inventors: Todd A. Peavey, Cambridge, MA (US); Sean T. Forde, Watertown, MA (US); Andrzej J. Chanduszko, Weymouth, MA (US); David J. Callaghan, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1559 days.

(21) Appl. No.: 10/396,253

(22) Filed: Mar. 25, 2003

(65) Prior Publication Data

US 2003/0225421 A1 Dec. 4, 2003

Related U.S. Application Data

(60) Provisional application No. 60/366,534, filed on Mar. 25, 2002.

(51) Int. Cl.
*A61B 17/08* (2006.01)
*A61D 1/00* (2006.01)
*A61B 17/00* (2006.01)

(52) U.S. Cl.
CPC ........... *A61B 17/0057* (2013.01); *A61B 17/083* (2013.01); *A61B 2017/00575* (2013.01); *A61B 2017/00592* (2013.01); *A61B 2017/00606* (2013.01); *A61B 2017/00867* (2013.01)

(58) Field of Classification Search
CPC .. A61B 17/0057; A61B 17/08; A61B 17/083; A61B 17/122; A61B 2017/00575–2017/00632; A61B 2017/00646–2017/00668
USPC ......... 606/151, 213, 215, 157, 158, 216–221, 606/139, 142, 143; 623/23.72; 24/67.1, 24/67.3, 67.9
See application file for complete search history.

(56) References Cited

U.S. PATENT DOCUMENTS

| 649,338 A | * | 5/1900 | McGill | 248/302 |
| 2,642,638 A | * | 6/1953 | Larrabee | 24/67.9 |

(Continued)

FOREIGN PATENT DOCUMENTS

| DE | 9413645 U1 | 10/1994 |
| DE | 196 04 817 | 8/1997 |

(Continued)

OTHER PUBLICATIONS

Stöckel, "Nitinol Medical Devices and Implants," SMST-2000 Conference Proceedings, 2001, pp. 531-541.

(Continued)

*Primary Examiner* — Katherine Rodjom
*Assistant Examiner* — Lindsey Bachman
(74) *Attorney, Agent, or Firm* — DLA Piper LLP (US)

(57) ABSTRACT

The present invention provides a patent foramen ovale (PFO) closure clip. The clips of the present invention include two closure members joined by at least two spaced central connecting members. Each of the at least two spaced central connecting members is attached to each closure member at a location on the periphery of the closure member. The clips are designed such that the at least two central connecting members extend through the inclined PFO tunnel and the two closure members compress the overlapping layers of septal tissue, i.e. septum primum and septum secundum, together to close the PFO tunnel. The clips of the present invention take various forms depending, in part, upon the distribution of force required to close a given PFO. Thus, in some embodiments, the closure members include arcuate peaks. In other embodiments, the closure members include loops. In still other embodiments, the closure members include prongs.

52 Claims, 5 Drawing Sheets

(56) References Cited

U.S. PATENT DOCUMENTS

| | | | | |
|---|---|---|---|---|
| 3,824,631 | A | 7/1974 | Burstein et al. | |
| 3,874,388 | A | 4/1975 | King et al. | |
| 3,875,648 | A | 4/1975 | Bone | 29/417 |
| 3,924,631 | A | 12/1975 | Mancusi, Jr. | |
| 4,006,747 | A | 2/1977 | Kronenthal et al. | 128/335 |
| 4,007,743 | A | 2/1977 | Blake | 128/334 |
| 4,149,327 | A | 4/1979 | Hammer et al. | |
| 4,425,908 | A | 1/1984 | Simon | 128/1 |
| 4,610,674 | A | 9/1986 | Suzuki et al. | |
| 4,626,245 | A | 12/1986 | Weinstein | |
| 4,693,249 | A | 9/1987 | Schenck et al. | |
| 4,696,300 | A | 9/1987 | Anderson | 128/334 |
| 4,710,181 | A | 12/1987 | Fuqua | |
| 4,710,192 | A | 12/1987 | Liotta et al. | |
| 4,738,666 | A | 4/1988 | Fuqua | |
| 4,836,204 | A | 6/1989 | Landymore et al. | 128/334 |
| 4,840,623 | A | 6/1989 | Quackenbush | |
| 4,902,508 | A | 2/1990 | Badylak et al. | |
| 4,915,107 | A | 4/1990 | Rebuffat et al. | 606/144 |
| 4,917,089 | A | 4/1990 | Sideris | |
| 4,921,479 | A | 5/1990 | Grayzel | |
| 4,956,178 | A | 9/1990 | Badylak et al. | |
| 5,021,059 | A | 6/1991 | Kensey et al. | 606/213 |
| 5,037,433 | A | 8/1991 | Wilk et al. | 606/139 |
| 5,041,129 | A | 8/1991 | Hayhurst et al. | 606/232 |
| 5,049,131 | A | 9/1991 | Deuss | |
| 5,078,736 | A | 1/1992 | Behl | |
| 5,106,913 | A | 4/1992 | Yamaguchi et al. | |
| 5,108,420 | A | 4/1992 | Marks | |
| 5,149,327 | A | 9/1992 | Oshiyama | |
| 5,163,131 | A | 11/1992 | Row et al. | |
| 5,167,363 | A | 12/1992 | Adkinson et al. | |
| 5,167,637 | A | 12/1992 | Okada et al. | |
| 5,171,259 | A * | 12/1992 | Inoue | 606/213 |
| 5,176,659 | A | 1/1993 | Mancini | |
| 5,192,301 | A | 3/1993 | Kamiya et al. | 606/213 |
| 5,222,974 | A | 6/1993 | Kensey et al. | 606/213 |
| 5,226,879 | A | 7/1993 | Ensminger et al. | |
| 5,236,440 | A | 8/1993 | Hlavacek | 606/219 |
| 5,245,023 | A | 9/1993 | Peoples et al. | |
| 5,245,080 | A | 9/1993 | Aubard et al. | |
| 5,250,430 | A | 10/1993 | Peoples et al. | |
| 5,257,637 | A | 11/1993 | El Gazayerli | 128/898 |
| 5,275,826 | A | 1/1994 | Badylak et al. | |
| 5,282,827 | A | 2/1994 | Kensey et al. | 606/215 |
| 5,284,488 | A | 2/1994 | Sideris | 606/213 |
| 5,304,184 | A | 4/1994 | Hathaway et al. | 606/144 |
| 5,312,341 | A | 5/1994 | Turi | |
| 5,312,435 | A | 5/1994 | Nash et al. | 606/213 |
| 5,316,262 | A | 5/1994 | Koebler | |
| 5,320,611 | A | 6/1994 | Bonutti et al. | |
| 5,334,217 | A | 8/1994 | Das | |
| 5,350,363 | A | 9/1994 | Goode et al. | |
| 5,354,308 | A | 10/1994 | Simon et al. | 606/198 |
| 5,364,356 | A | 11/1994 | Hofling | |
| 5,411,481 | A | 5/1995 | Allen et al. | 606/144 |
| 5,413,584 | A | 5/1995 | Schulze | 606/219 |
| 5,417,699 | A | 5/1995 | Klein et al. | 606/144 |
| 5,425,744 | A | 6/1995 | Fagan et al. | |
| 5,433,727 | A | 7/1995 | Sideris | 606/213 |
| 5,451,235 | A | 9/1995 | Lock et al. | |
| 5,453,099 | A | 9/1995 | Lee et al. | |
| 5,478,353 | A | 12/1995 | Yoon | 606/213 |
| 5,480,353 | A | 1/1996 | Garza, Jr. | |
| 5,480,424 | A | 1/1996 | Cox | |
| 5,486,193 | A | 1/1996 | Bourne et al. | |
| 5,507,811 | A | 4/1996 | Koike et al. | 623/11 |
| 5,534,432 | A | 7/1996 | Peoples et al. | |
| 5,540,712 | A | 7/1996 | Kleshinski et al. | 606/198 |
| 5,562,632 | A | 10/1996 | Davila et al. | |
| 5,577,299 | A | 11/1996 | Thompson et al. | |
| 5,601,571 | A | 2/1997 | Moss | 606/139 |
| 5,603,703 | A | 2/1997 | Elsberry et al. | |
| 5,618,311 | A | 4/1997 | Gryskiewicz | 606/216 |
| 5,620,461 | A | 4/1997 | Muijs Van De Moer et al. | |
| 5,626,599 | A | 5/1997 | Bourne et al. | |
| 5,634,936 | A | 6/1997 | Linden et al. | 606/213 |
| 5,649,950 | A | 7/1997 | Bourne et al. | |
| 5,649,959 | A | 7/1997 | Hannam et al. | |
| 5,663,063 | A | 9/1997 | Peoples et al. | |
| 5,683,411 | A | 11/1997 | Kavteladze et al. | 606/200 |
| 5,690,674 | A | 11/1997 | Diaz | |
| 5,693,085 | A | 12/1997 | Buirge et al. | |
| 5,702,421 | A | 12/1997 | Schneidt | 606/213 |
| 5,709,707 | A | 1/1998 | Lock et al. | |
| 5,713,864 | A | 2/1998 | Verkaart | |
| 5,717,259 | A | 2/1998 | Schexnayder | |
| 5,720,754 | A | 2/1998 | Middleman et al. | 606/127 |
| 5,725,552 | A | 3/1998 | Kotula et al. | 606/213 |
| 5,733,294 | A | 3/1998 | Forber et al. | 606/151 |
| 5,733,337 | A | 3/1998 | Carr, Jr. et al. | |
| 5,741,297 | A | 4/1998 | Simon | 606/213 |
| 5,772,641 | A | 6/1998 | Wilson | |
| 5,776,162 | A | 7/1998 | Kleshinski | 606/198 |
| 5,776,183 | A | 7/1998 | Kanesaka et al. | |
| 5,797,960 | A | 8/1998 | Stevens et al. | 606/213 |
| 5,800,516 | A | 9/1998 | Fine et al. | |
| 5,810,884 | A | 9/1998 | Kim | 606/213 |
| 5,820,594 | A | 10/1998 | Fontirroche et al. | |
| 5,823,956 | A | 10/1998 | Roth et al. | 600/374 |
| 5,829,447 | A | 11/1998 | Stevens et al. | 128/898 |
| 5,853,420 | A | 12/1998 | Chevillon et al. | |
| 5,853,422 | A | 12/1998 | Huebsch et al. | |
| 5,855,614 | A | 1/1999 | Stevens et al. | 623/11 |
| 5,861,003 | A | 1/1999 | Latson et al. | 606/213 |
| 5,865,791 | A | 2/1999 | Whayne et al. | |
| 5,879,366 | A | 3/1999 | Shaw et al. | 606/213 |
| 5,893,856 | A | 4/1999 | Jacob et al. | 606/151 |
| 5,902,287 | A | 5/1999 | Martin | |
| 5,902,319 | A | 5/1999 | Daley | 606/219 |
| 5,904,703 | A | 5/1999 | Gilson | 606/213 |
| 5,919,200 | A | 7/1999 | Stambaugh et al. | 606/159 |
| 5,924,424 | A | 7/1999 | Stevens et al. | 128/898 |
| 5,928,250 | A | 7/1999 | Koike et al. | |
| 5,944,691 | A | 8/1999 | Querns et al. | |
| 5,944,738 | A | 8/1999 | Amplatz et al. | |
| 5,955,110 | A | 9/1999 | Patel et al. | |
| 5,976,174 | A | 11/1999 | Ruiz | |
| 5,980,505 | A | 11/1999 | Wilson | |
| 5,989,268 | A | 11/1999 | Pugsley, Jr. et al. | 606/144 |
| 5,993,475 | A | 11/1999 | Lin et al. | 606/213 |
| 5,993,844 | A | 11/1999 | Abraham et al. | |
| 5,997,575 | A | 12/1999 | Whitson et al. | |
| 6,010,517 | A | 1/2000 | Baccaro | |
| 6,015,417 | A * | 1/2000 | Reynolds, Jr. | 606/151 |
| 6,019,753 | A | 2/2000 | Pagan | |
| 6,024,756 | A | 2/2000 | Huebsch et al. | 606/213 |
| 6,027,519 | A | 2/2000 | Stanford | |
| 6,030,007 | A | 2/2000 | Bassily et al. | |
| 6,056,760 | A | 5/2000 | Koike et al. | 606/148 |
| 6,071,998 | A | 6/2000 | Muller et al. | |
| 6,077,281 | A * | 6/2000 | Das | 606/151 |
| 6,077,291 | A | 6/2000 | Das | |
| 6,077,880 | A | 6/2000 | Castillo et al. | |
| 6,079,414 | A | 6/2000 | Roth | 128/898 |
| 6,080,182 | A | 6/2000 | Shaw et al. | 606/213 |
| 6,096,347 | A | 8/2000 | Geddes et al. | |
| 6,106,913 | A | 8/2000 | Scardino et al. | |
| 6,113,609 | A | 9/2000 | Adams | |
| 6,117,159 | A | 9/2000 | Huebsch et al. | 606/213 |
| 6,126,686 | A | 10/2000 | Badylak et al. | |
| 6,132,438 | A | 10/2000 | Fleischman et al. | 606/139 |
| 6,143,037 | A | 11/2000 | Goldstein et al. | |
| 6,152,144 | A | 11/2000 | Lesh et al. | |
| 6,165,183 | A | 12/2000 | Kuehn et al. | 606/139 |
| 6,165,204 | A | 12/2000 | Levinson et al. | 606/232 |
| 6,168,588 | B1 | 1/2001 | Wilson | |
| 6,171,320 | B1 * | 1/2001 | Monassevitch | 606/151 |
| 6,171,329 | B1 | 1/2001 | Shaw et al. | |
| 6,174,322 | B1 | 1/2001 | Schneidt | |
| 6,174,330 | B1 | 1/2001 | Stinson | |
| 6,183,443 | B1 | 2/2001 | Kratoska et al. | |
| 6,187,039 | B1 | 2/2001 | Hiles et al. | |
| 6,190,353 | B1 | 2/2001 | Makower et al. | |

(56) References Cited

U.S. PATENT DOCUMENTS

| | | | |
|---|---|---|---|
| 6,190,357 B1 | 2/2001 | Ferrari et al. | |
| 6,197,016 B1 | 3/2001 | Fourkas et al. | |
| 6,199,262 B1 | 3/2001 | Martin | |
| 6,206,895 B1 | 3/2001 | Levinson | 606/144 |
| 6,206,907 B1 | 3/2001 | Marino et al. | |
| 6,214,029 B1 | 4/2001 | Thill et al. | |
| 6,217,590 B1 | 4/2001 | Levinson | 606/142 |
| 6,221,092 B1 | 4/2001 | Koike et al. | |
| 6,227,139 B1 | 5/2001 | Nguyen et al. | |
| 6,228,097 B1 | 5/2001 | Levinson et al. | 606/142 |
| 6,231,561 B1 | 5/2001 | Frazier et al. | |
| 6,245,080 B1 | 6/2001 | Levinson | 606/144 |
| 6,245,537 B1 | 6/2001 | Williams et al. | |
| 6,261,309 B1 | 7/2001 | Urbanski | |
| 6,265,333 B1 | 7/2001 | Dzenis et al. | |
| 6,270,515 B1 | 8/2001 | Linden et al. | 606/213 |
| 6,277,138 B1 | 8/2001 | Levinson et al. | 606/200 |
| 6,277,139 B1 | 8/2001 | Levinson et al. | 606/200 |
| 6,287,317 B1 | 9/2001 | Makower et al. | 606/153 |
| 6,290,674 B1 | 9/2001 | Roue et al. | 604/107 |
| 6,299,635 B1 | 10/2001 | Frantzen | |
| 6,306,150 B1 | 10/2001 | Levinson | 606/158 |
| 6,306,424 B1 | 10/2001 | Vyakarnam et al. | |
| 6,312,443 B1 | 11/2001 | Stone | |
| 6,312,446 B1 | 11/2001 | Huebsch et al. | |
| 6,315,791 B1 | 11/2001 | Gingras et al. | |
| 6,316,262 B1 | 11/2001 | Huisman et al. | |
| 6,319,263 B1 | 11/2001 | Levinson | 606/144 |
| 6,322,548 B1 | 11/2001 | Payne et al. | |
| 6,328,727 B1 | 12/2001 | Frazier et al. | |
| 6,334,872 B1 | 1/2002 | Termin et al. | |
| 6,342,064 B1 | 1/2002 | Koike et al. | |
| 6,344,048 B1 | 2/2002 | Chin et al. | |
| 6,344,049 B1 | 2/2002 | Levinson et al. | 606/200 |
| 6,346,074 B1 | 2/2002 | Roth | |
| 6,348,041 B1 | 2/2002 | Klint | 600/585 |
| 6,352,552 B1 | 3/2002 | Levinson et al. | 623/1.15 |
| 6,355,052 B1 * | 3/2002 | Neuss et al. | 606/213 |
| 6,356,782 B1 | 3/2002 | Sirimanne et al. | |
| 6,358,238 B1 | 3/2002 | Sherry | |
| 6,364,853 B1 | 4/2002 | French et al. | 604/35 |
| 6,371,904 B1 * | 4/2002 | Sirimanne et al. | 600/3 |
| 6,375,625 B1 | 4/2002 | French et al. | 600/573 |
| 6,375,671 B1 | 4/2002 | Kobayashi et al. | |
| 6,379,342 B1 | 4/2002 | Levinson | 604/310 |
| 6,379,368 B1 | 4/2002 | Corcoran et al. | |
| 6,387,104 B1 | 5/2002 | Pugsley, Jr. et al. | 606/139 |
| 6,398,796 B2 | 6/2002 | Levinson | 606/144 |
| 6,402,772 B1 | 6/2002 | Amplatz et al. | |
| 6,419,669 B1 | 7/2002 | Frazier et al. | |
| 6,426,145 B1 | 7/2002 | Moroni | |
| 6,436,088 B2 | 8/2002 | Frazier et al. | |
| 6,440,152 B1 | 8/2002 | Gainor et al. | 606/213 |
| 6,450,987 B1 | 9/2002 | Kramer | |
| 6,460,749 B1 | 10/2002 | Levinson et al. | 227/180.1 |
| 6,482,224 B1 | 11/2002 | Michler et al. | |
| 6,488,706 B1 | 12/2002 | Solymar | 623/3.1 |
| 6,494,846 B1 | 12/2002 | Margolis | |
| 6,494,888 B1 | 12/2002 | Laufer et al. | 606/153 |
| 6,508,828 B1 | 1/2003 | Akerfeldt et al. | |
| 6,514,515 B1 | 2/2003 | Williams | |
| 6,537,286 B2 * | 3/2003 | Acampora et al. | 606/151 |
| 6,548,569 B1 | 4/2003 | Williams et al. | |
| 6,551,303 B1 | 4/2003 | Van Tassel et al. | |
| 6,551,344 B2 | 4/2003 | Thill | |
| 6,585,719 B2 | 7/2003 | Wang | |
| 6,585,755 B2 | 7/2003 | Jackson et al. | |
| 6,596,013 B2 | 7/2003 | Yang et al. | |
| 6,599,448 B1 | 7/2003 | Ehrhard, Jr. et al. | |
| 6,610,764 B1 | 8/2003 | Martin et al. | |
| 6,623,508 B2 | 9/2003 | Shaw et al. | |
| 6,623,518 B2 | 9/2003 | Thompson et al. | |
| 6,626,936 B2 | 9/2003 | Stinson | |
| 6,629,901 B2 | 10/2003 | Huang | |
| 6,666,861 B1 | 12/2003 | Grabek | |
| 6,669,722 B2 | 12/2003 | Chen et al. | |
| 6,689,589 B2 | 2/2004 | Huisman et al. | |
| 6,712,804 B2 | 3/2004 | Roue et al. | |
| 6,712,836 B1 | 3/2004 | Berg et al. | |
| 6,726,696 B1 | 4/2004 | Houser et al. | |
| 6,828,357 B1 | 12/2004 | Martin et al. | |
| 6,838,493 B2 | 1/2005 | Williams et al. | |
| 6,867,247 B2 | 3/2005 | Williams et al. | |
| 6,867,248 B1 | 3/2005 | Martin et al. | |
| 6,867,249 B2 | 3/2005 | Lee et al. | |
| 6,911,037 B2 * | 6/2005 | Gainor et al. | 606/213 |
| 6,921,410 B2 | 7/2005 | Porter | |
| 7,097,653 B2 * | 8/2006 | Freudenthal et al. | 606/213 |
| 2001/0010481 A1 | 8/2001 | Blanc et al. | |
| 2001/0014800 A1 | 8/2001 | Frazier et al. | |
| 2001/0025132 A1 | 9/2001 | Alferness et al. | |
| 2001/0034537 A1 | 10/2001 | Shaw et al. | |
| 2001/0034567 A1 | 10/2001 | Allen et al. | |
| 2001/0037129 A1 | 11/2001 | Thill | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | |
| 2002/0010481 A1 | 1/2002 | Jayaraman | |
| 2002/0019648 A1 | 2/2002 | Akerfeldt et al. | |
| 2002/0022859 A1 | 2/2002 | Hogendijk | |
| 2002/0022860 A1 | 2/2002 | Borillo et al. | |
| 2002/0026208 A1 | 2/2002 | Roe et al. | |
| 2002/0029048 A1 | 3/2002 | Miller | 606/138 |
| 2002/0032459 A1 | 3/2002 | Horzewski et al. | |
| 2002/0032462 A1 | 3/2002 | Houser et al. | 606/213 |
| 2002/0034259 A1 | 3/2002 | Tada | |
| 2002/0035374 A1 | 3/2002 | Borillo et al. | |
| 2002/0043307 A1 | 4/2002 | Ishida et al. | 148/411 |
| 2002/0049457 A1 | 4/2002 | Kaplan et al. | |
| 2002/0052572 A1 | 5/2002 | Franco et al. | |
| 2002/0058989 A1 | 5/2002 | Chen et al. | |
| 2002/0077555 A1 | 6/2002 | Schwartz | 600/486 |
| 2002/0095174 A1 | 7/2002 | Tsugita et al. | |
| 2002/0096183 A1 | 7/2002 | Stevens et al. | |
| 2002/0099389 A1 | 7/2002 | Michler et al. | 606/139 |
| 2002/0099390 A1 | 7/2002 | Kaplan et al. | |
| 2002/0103492 A1 | 8/2002 | Kaplan et al. | |
| 2002/0107531 A1 | 8/2002 | Schreck et al. | |
| 2002/0111537 A1 | 8/2002 | Taylor et al. | |
| 2002/0111637 A1 | 8/2002 | Kaplan et al. | |
| 2002/0111647 A1 | 8/2002 | Khairkhahan et al. | |
| 2002/0120323 A1 | 8/2002 | Thompson et al. | |
| 2002/0128680 A1 | 9/2002 | Pavlovic | |
| 2002/0129819 A1 | 9/2002 | Feldman et al. | 128/831 |
| 2002/0164729 A1 | 11/2002 | Skraly et al. | |
| 2002/0169377 A1 | 11/2002 | Khairkhahan et al. | |
| 2002/0183786 A1 | 12/2002 | Girton | 606/213 |
| 2002/0183787 A1 | 12/2002 | Wahr et al. | |
| 2002/0183823 A1 | 12/2002 | Pappu | |
| 2002/0198563 A1 | 12/2002 | Gainor et al. | |
| 2003/0004533 A1 | 1/2003 | Dieck et al. | |
| 2003/0023266 A1 | 1/2003 | Welch et al. | |
| 2003/0028213 A1 | 2/2003 | Thill et al. | |
| 2003/0045893 A1 | 3/2003 | Ginn | |
| 2003/0050665 A1 | 3/2003 | Ginn | |
| 2003/0055455 A1 | 3/2003 | Yang et al. | |
| 2003/0057156 A1 | 3/2003 | Peterson et al. | |
| 2003/0059640 A1 | 3/2003 | Marton et al. | |
| 2003/0065379 A1 | 4/2003 | Babbas et al. | |
| 2003/0100920 A1 | 5/2003 | Akin et al. | |
| 2003/0120337 A1 | 6/2003 | Van Tassel et al. | |
| 2003/0139819 A1 | 7/2003 | Beer et al. | |
| 2003/0171774 A1 | 9/2003 | Freudenthal et al. | |
| 2003/0191495 A1 | 10/2003 | Ryan et al. | |
| 2003/0195530 A1 | 10/2003 | Thill | |
| 2003/0204203 A1 | 10/2003 | Khairkhahan et al. | |
| 2004/0044361 A1 | 3/2004 | Frazier et al. | |
| 2004/0073242 A1 | 4/2004 | Chanduszko | |
| 2004/0176799 A1 | 9/2004 | Chanduszko et al. | |
| 2004/0210301 A1 | 10/2004 | Obermiller | |
| 2004/0234567 A1 | 11/2004 | Dawson | |

(56) References Cited

U.S. PATENT DOCUMENTS

| | | |
|---|---|---|
| 2005/0025809 A1 | 2/2005 | Hasirci et al. |
| 2005/0043759 A1 | 2/2005 | Chanduszko |
| 2005/0113868 A1* | 5/2005 | Devellian et al. ............ 606/213 |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2007/0010851 A1 | 1/2007 | Chanduszko et al. |
| 2007/0167981 A1 | 7/2007 | Opolski |

FOREIGN PATENT DOCUMENTS

| | | | |
|---|---|---|---|
| EP | 0362113 | 4/1990 | |
| EP | 0474887 A1 | 3/1992 | |
| EP | 0839549 A1 | 5/1998 | |
| EP | 0 861 632 | 9/1998 | |
| EP | 1 013 227 | 6/2000 | ............ A61B 17/00 |
| EP | 1 046 375 | 10/2000 | |
| EP | 1 222 897 | 7/2002 | |
| WO | WO 96/25179 | 8/1996 | |
| WO | WO 96/31157 | 10/1996 | |
| WO | WO-98/07375 | 2/1998 | |
| WO | WO-98/08462 | 3/1998 | |
| WO | WO-98/16174 | 4/1998 | |
| WO | WO-98/29026 | 7/1998 | |
| WO | WO-98/51812 | 11/1998 | |
| WO | WO-99/05977 | 2/1999 | |
| WO | WO-98/18864 | 4/1999 | |
| WO | WO-99/18862 | 4/1999 | |
| WO | WO-99/18864 | 4/1999 | |
| WO | WO-99/18870 | 4/1999 | |
| WO | WO-99/18871 | 4/1999 | |
| WO | WO-99/30640 | 6/1999 | |
| WO | WO-99/39646 | 8/1999 | |
| WO | WO 00/27292 | 5/2000 | ............ A61B 17/08 |
| WO | WO 00/44428 | 8/2000 | |
| WO | WO-01/08600 | 2/2001 | |
| WO | WO-01/19256 | 3/2001 | |
| WO | WO-01/21247 | 3/2001 | |
| WO | WO-01/28432 | 4/2001 | |
| WO | WO-01/30268 | 5/2001 | |
| WO | WO 01/49185 | 7/2001 | ............ A61B 17/00 |
| WO | WO-01/78596 | 10/2001 | |
| WO | WO-01/93783 | 12/2001 | |
| WO | WO-02/17809 | 3/2002 | |
| WO | WO 02/24106 | 3/2002 | |
| WO | WO-03/024337 | 3/2003 | |
| WO | WO-03/053493 | 7/2003 | |
| WO | WO-03/53493 A2 | 7/2003 | |
| WO | WO-03/059152 | 7/2003 | |
| WO | WO 03/077733 | 9/2003 | |
| WO | WO-03/082076 | 10/2003 | |
| WO | WO-03/103476 | 12/2003 | |
| WO | WO-03/103476 A2 | 12/2003 | |
| WO | WO-2004/032993 | 4/2004 | |
| WO | WO-2004/037333 | 5/2004 | |
| WO | WO-2004/043266 | 5/2004 | |
| WO | WO-2004/043508 | 5/2004 | |
| WO | WO-2004/052213 | 6/2004 | |
| WO | WO-2005/006990 | 1/2005 | |
| WO | WO-2005/018728 | 3/2005 | |
| WO | WO-2005/027752 | 3/2005 | |
| WO | WO-2005/074813 | 8/2005 | |
| WO | WO-2005/092203 | 10/2005 | |
| WO | WO-2005/110240 | 11/2005 | |
| WO | WO-2005/112779 | 12/2005 | |
| WO | WO-2006/036837 | 4/2006 | |
| WO | WO-2006/102213 | 9/2006 | |

OTHER PUBLICATIONS

SMST-2000, "Proceedings of the International Conference on Shape Memory and Superelastic Technologies," Apr. 30, to May 4, 2000, Asilomar Conference Center.

Ruiz et al. "the Puncture Technique: A New Method for Transcatheter Closure of Patent Foramen Ovale," Catheterization and Cardiovascular Interventions 53, Wiley-Liss, Inc., 2001, pp. 369-372.
International Search Report, International Application No. PCT/US03/17390, mailed on Oct. 6, 2003, 4 pgs.
Nat'l Aeronautics and Space Administration, "55-Nitinol—The Alloy with a Memory: Its Physical Metallurgy, Properties, and Applications," A Report, pp. 24-25.
Kimura, A., et al., "Effects of Neutron Irradiation on the Transformation Behavior in Ti—Ni Alloys," Abstract, Proceedings of the Int'l Conf. On Mariensitic Transformations (1992) pp. 935-940.
Ramanathan, G., et al., "Experimental and Computational Methods for Shape Memory Alloys," 15$^{th}$ ASCE Engineering Mechanics Conf., Jun. 2-5, 2003.
Shabalovskaya, S., "Surface, corrosion and biocompatibility aspects of Nitinol as an implant material," Bio-Medical materials and Engineering, (2002) vol. 12, pp. 69-109.
Uchil, J. "Shape Memory Alloys—Characterization Techniques," Pramana—Journal of Physics, (2002) vol. 58, Nos. 5 & 6, pp. 1131-1139.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 04781644.2, mailed Aug. 23, 2007 (3 pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (4 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/USO4/026998, mailed Apr. 22, 2005 (5 pgs).
International Search Report, International Application No. PCT/USO4/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US06/009978, mailed Jul. 13, 2006 (2 pgs).
International Search Report, International Application No. PCT/US2007/065526, mailed Aug. 8, 2007 (5 pgs).
International Search Report, International Application No. PCT/US2007/065541, mailed Aug. 7, 2007 (3 pgs).
International Search Report, International Application No. PCT/US97/14822, mailed Feb. 20, 1998 (2 pgs).

(56) References Cited

OTHER PUBLICATIONS

International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Klima, U., "Magnetic Vascular Port in Minimally Invasive Direct Coronary Artery Bypass Grafting," Circulation, 2004, II-55-II-60.
Meier, MD, Bernhard et al., "Contemporary Management of Patent Foramen Ovale," American Heart Association, Inc., Circulation, 2003, vol. 107, pp. 5-9.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.
European Examination Report, European Application No. 03779297.5, mailed arch 15, 2007 (6 Pages).
International Search Report for International Patent Application No. PCT/AU03/00759, filed Jun. 19, 2003.
International Search Report, International Application No. PCT/US05/34276, mailed Oct. 9, 2007.
International Search Report, International Application No. PCT/US07/065546, mailed Oct. 29, 2007. 4 pages.
European Search Report, European Application No. 03729663.9, mailed Feb. 20, 2008 (3 Pages).
European Search Report, European Application No. 03716812.7, mailed Mar. 14, 2008 (3 Pages).
International Search Report, International Application No. PCT/US07/065546, mailed Oct. 29, 2007 (4 pages).

\* cited by examiner

PATENT FORAMEN OVALE (PFO) CLOSURE CLIPS

The instant patent application claims priority to U.S. Provisional Patent Application 60/366,534, filed Mar. 25, 2002, which is incorporated herein by reference.

FIELD OF THE INVENTION

The present invention relates to devices and methods that are used to close septal openings. In particular, this invention is directed to devices and methods that are used to close a patent foramen ovale (PFO) in the septum between the left atrium and right atrium.

BACKGROUND OF THE INVENTION

A PFO, illustrated in FIG. 1, is a persistent, one-way, usually flap-like opening in the wall between the right atrium 10 and left atrium 12 of the heart. Because left atrial (LA) pressure is normally higher than right atrial (RA) pressure, the flap usually stays closed. Under certain conditions, however, right atrial pressure can exceed left atrial pressure, which creates the possibility that blood could pass from the right atrium to the left atrium and allow blood clots to enter the systemic circulation. It is desirable that this circumstance be eliminated.

The foramen ovale serves a desired purpose when a fetus is gestating in utero. Since blood is oxygenated through the umbilical chord, and not through the developing lungs, the circulatory system of a heart in a fetus allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another cause of ischemic stroke. While there is currently no definitive proof for a cause-effect relationship, many studies have confirmed a strong association between the presence of a PFO and the risk for paradoxical embolism or stroke. In addition, there is significant evidence that patients with PFO who have had a cerebral vascular event are at increased risk for future, recurrent cerebrovascular events.

Accordingly, patients with an increased future risk are considered for prophylactic medical therapy to reduce the risk of a recurrent embolic event. These patients are commonly treated with oral anticoagulants, which have the potential for adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close the PFO. The surgery would typically include suturing a PFO closed by attaching septum secundum to septum primum. This sutured attachment can be accomplished with either an interrupted or a continuous stitch and is a common way a surgeon shuts a PFO under direct visualization.

Umbrella devices and a variety of other similar mechanical closure designs, developed initially for percutaneous closure of atrial septal defects (ASDs), have been used in some instances to close PFOs. These devices have the potential to allow patients to avoid the potential side effects often associated with anticoagulation therapies and the risks of invasive surgery. However, umbrella devices and the like that are designed for ASDs are not optimally suited for use as a PFO closure device.

Currently available designs of septal closure devices present drawbacks, including that the implantation procedure is technically complex. Additionally, there are not insignificant complications due to thrombus, fractures of the components, conduction system disturbances, perforations of heart tissue, and residual leaks. Many devices have high septal profile and may include large masses of foreign material, which may lead to unfavorable body adaptation of a device. Since ASD devices are designed to occlude a hole, many lack anatomic conformability to the PFO flap-like anatomy. That is, when inserting an ASD device to close a PFO, the narrow opening and the thin flap may form impediments to proper deployment. Even if an occlusive seal is formed, the device may be deployed in the heart on an angle, which could leave some components not securely seated against the septum. Finally, some septal closure devices are complex to manufacture, which may result in lack of consistency in product performance.

The present invention is designed to address these and other deficiencies of the prior art septal closure devices.

SUMMARY OF THE INVENTION

The present invention provides patent foramen ovale (PFO) closure clips. The clips of the present invention include two closure members joined by at least two spaced central connecting members. Each of the at least two spaced central connecting members is attached to each closure member at a location on the periphery of the closure member. The clips are designed such that the at least two central connecting members extend through the inclined PFO tunnel and the two closure members compress the overlapping layers of septal tissue, i.e. septum primum and septum secundum, together to close the PFO tunnel.

The clips of the present invention may be formed of various materials. In at least some embodiments, the clips are formed of metals, nonmetallic materials, bioabsorbable polymers, spring steel, shape memory materials, bioabsorbable shape memory polymers, or combinations thereof.

The clips of the present invention take various forms depending, in part, upon the distribution of force required to close a given PFO. Thus, in some embodiments, the closure members include arcuate peaks. In other embodiments, the closure members include loops. In still other embodiments, the closure members include prongs. In yet other embodiments, the closure members include centering elements.

In at least some embodiments, the clips of the present invention are repositionable and/or retrievable. In some embodiments, at least one of the closure members includes a tissue scaffold.

BRIEF DESCRIPTION OF THE DRAWINGS

FIG. 3b illustrates a device disposed in a PFO;

DESCRIPTION OF PREFERRED EMBODIMENTS

Figure 1:
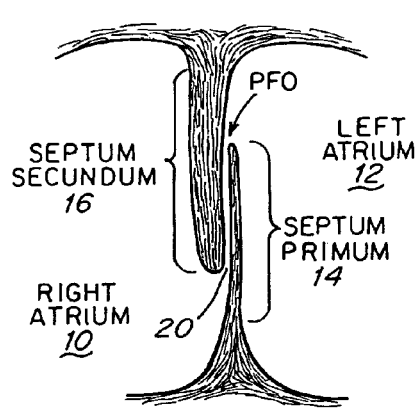
FIG. 1 is a diagrammatic sectional view of a Patent Foramen Ovale (PFO) between the right atrium and the left atrium.

The clip devices of the present invention are intended to clip septum primum to septum secundum to thereby minimize the flow of blood between the right and left atria. The clip devices assist in reducing the risk of stroke by preventing the passage of embolic particles from the right atrium to the left atrium through a PFO. To accomplish this, the clip devices apply a compressive force to the overlapping layers of septal tissue between the right and left atria, i.e. septum primum and septum secundum. In at least some embodiments, the applied compressive force "pulls" the more flexible septum primum toward septum secundum, thereby closing the PFO without significantly distorting the septum, as occurs with many of the septal closure devices of the prior art. In this application, compressive force is intended to include force sufficient to bring septum primum and septum secundum together to provide a closing effect. In some embodiments, the clip provides mechanical closure at enough points of contact along the PFO that the single largest remaining conduit is reduced to a size deemed small enough to block stroke-inducing embolic particles from crossing through the PFO tunnel. In other embodiments, the clip provides substantially complete closure along the entire PFO length. Because the clip devices of the present invention do not distort the defect, the overlapping layers of septal tissues may themselves be used to close the defect as they are compressed by the clip device. Accordingly, in at least some embodiments, the application of a compressive force to the septal tissues using the clip devices of the present invention may ultimately induce anatomical closure of septum primum and septum secundum (i.e. septum primum and septum secundum will fuse together by natural processes).

The clip devices of the present invention may be formed of metal wire, nonmetallic materials, bioabsorbable polymers, spring steel, shape memory materials (e.g. nitinol), bioabsorbable shape memory polymers, or combinations of the foregoing materials. In some embodiments, the clip devices are formed of a single piece of material, while in other embodiments, the clip devices are formed of multiple pieces of material.

In particular embodiments, the clip devices are formed of shape memory material (e.g. nitinol), which allows the clips to resume and maintain their intended shape following deployment in vivo. A clip according to the present invention may use the thermal shape memory properties of a shape memory material, the superelastic properties of a shape memory material, or some combination of the two. In other particular embodiments, the clip devices are cut into their desired shapes from sheets of material, including bioabsorbable shape memory polymers. Those skilled in the art will recognize that the device could be made of a combination of materials. Those of skill in the art will be able to identify biocompatible clip materials suited for particular applications, and the manufacturing techniques that would be used to configure the material into specific clip designs.

In at least some embodiments, the clip devices of the present invention include first and second closure members connected by at least two spaced central connecting members. Each central connecting member is attached to each closure member at a point on the periphery of the closure member. The central connecting member may be any strand of material, e.g. a wire or portion of wire, that connects the closure members. The connecting members are intended to pass through the PFO tunnel. After deployment into the heart, the second closure member is located in the left atrium and the first closure member is located in the right atrium, such that the central connecting members extend through the PFO tunnel, as described below for the various embodiments of the present invention.

The first and second closure members may be constituted of a material or be configured to apply a compressive force to the overlapping layers of septal tissue. Further, the movement of the at least two spaced central connecting members extending through the PFO tunnel may be limited by the edges of the PFO tunnel (which is usually between 1 mm and 20 mm wide), thereby ensuring the clip device remains horizontally centered across the defect and consistently applies compressive force to the septal tissues at the locations necessary to effect closure of the defect. This accurate and consistent application of localized force permits the use of a smaller closure device.

In some embodiments, the clip devices of the present invention include only one closure member and at least one connecting member. The connecting member passes through the PFO tunnel and secures the closure member in place.

The closure members of the clip devices may take various forms depending, in part, upon the distribution of force desired to effect closure of a given defect. In this application, the term defect is applied to any anatomical configuration requiring treatment. In particular, the defect can be a PFO which may allow, or allows, blood to flow from the right atrium to the left atrium. The shape of each closure member determines the location(s) at which the compressive force is applied to the overlapping layers of septal tissue.

In some embodiments, the compressive force is concentrated at the center of the longitudinal distance of the PFO tunnel. In other embodiments, the compressive force is distributed along the length of the defect. In still other embodiments, the compressive force is applied toward the edges of the PFO defect. Of course, the force may be a combination of the above-described forces. In at least some embodiments, the closure devices of the present invention are low profile devices, i.e. the closure members contact the septal tissue both inferior to and superior to the PFO tunnel entrance in the left atrium or the right atrium or both. The device may include configurations that are centered horizontally or vertically in the PFO. These and other embodiments of the clip devices of the present invention are described below. In the Figures, the directional indications, e.g. downward and upward, are meant to facilitate understanding of the invention and are not intended to limit the invention in any manner.

Figure 2A:
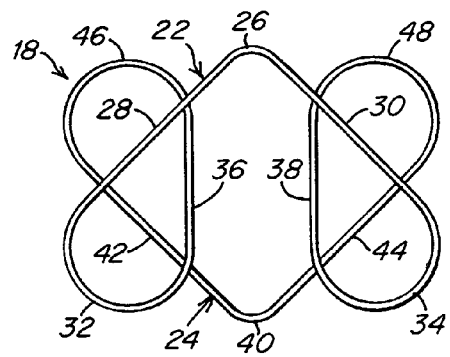
FIGS. 2a and 2b are a front elevational view and a side view, respectively, of a PFO closure clip according to a first embodiment of the present invention.
Figure 2B:
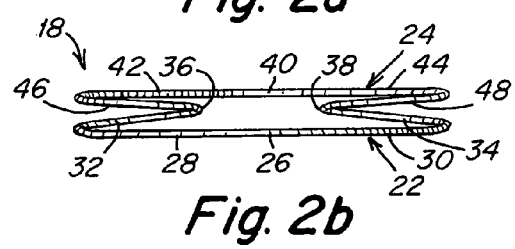
Figure 3A:
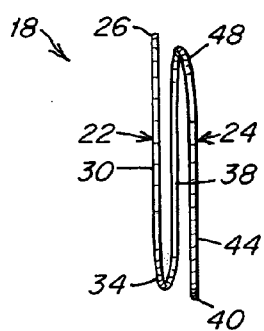
FIGS. 3a and 3b are side elevational views of the PFO closure clip of FIG. 2.
Figure 3B:
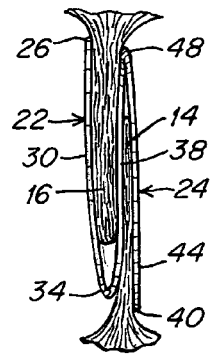
Figure 4:
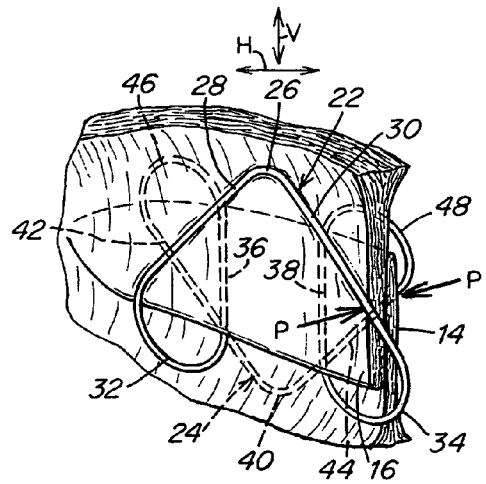
FIG. 4 is a front elevational view of the PFO closure clip of FIG. 2 in place in a PFO as seen from the right atrium.

Referring to FIGS. 2-4, a first embodiment of the PFO closure clip of the present invention, indicated generally at 18, is designed to extend through the inclined PFO tunnel 20 between septum secundum 16 and septum primum 14 to engage the outer surfaces of septum secundum 16 and septum primum 14 in both the left and right atria. As shown in FIG. 3b, the compressive force applied by the closure clip 18 forces the layers of septal tissue together to close the PFO tunnel 20, thereby inducing anatomical closure of septum primum and septum secundum.

The clip 18 includes a first closure member 22 that overlies a second closure member 24. The first and second closure members 22 and 24 of the clip 18 are biased toward one another and, as shown in FIG. 2, are connected at their peripheries by connecting strands 36 and 38. The connecting strands are relatively straight and are configured to pass through the PFO tunnel. In other embodiments, there may be a slight curve to the connecting strands. The first closure member includes an arcuate peak 26 that joins two elongate side strands 28 and 30, both of which are oriented away from the peak 26 to form, as illustrated, a triangle. The angle of the peak 26 is broad enough to allow the strands 28 and 30 to extend over a sufficient amount of the PFO but not so much as to interfere with the function of the heart. Of course, the peak 26 may be designed with a large angle, e.g. greater than 90° and the side strands 28 and 30 may be rounded to cover the PFO closure. As described below, smaller angles are also contemplated according to this invention. At their lowermost extremities side strands 28 and 30 are looped to provide spaced bottom loops 32 and 34 at a radius sufficient to direct the wires into the PFO tunnel for the first closure member. Loops 32 and 34 extend into straight, spaced, elongate connecting strands 36 and 38, respectively, which connect the first closure member 22 to the second closure member 24. As previously indicated, the straight, spaced, elongate connecting strands 36 and 38 are designed to extend through the inclined PFO tunnel 20 between septum primum and septum secundum.

The second closure member 24 is substantially identical in construction to the first closure member 22 but is oriented in a reverse manner to the first closure member 22. The second closure member includes an arcuate peak 40, aligned with but spaced opposite to the arcuate peak 26, that joins two outwardly angled, elongate side strands 42 and 44. At their uppermost extremities, elongate side strands 42 and 44 are looped to provide spaced top loops 46 and 48, respectively, for the second closure member 24, which are substantially aligned with but spaced opposite to bottom loops 32 and 34.

Loops 46 and 48 extend into straight, spaced, elongate, connecting strands 36 and 38, respectively. The same configuration adjustments may be made to the second closure member as suggested for the first closure member.

FIGS. 3a, 3b, and 4 show the clip 18 in place to close a PFO. Clip 18 may be elongated and deployed through a catheter. The catheter enters the right atrium and is inserted through the PFO tunnel into the left atrium. Closure member 24 is then ejected into the left atrium, where it resumes the shape shown in FIG. 4. The catheter is then withdrawn through the PFO tunnel into the right atrium such that spaced, elongate connecting strands 36 and 38 are deployed and extend through the PFO tunnel. Finally, closure member 22 is deployed into the right atrium, where it resumes the shape shown in FIG. 4. When so deployed, closure members 22 and 24 apply a compressive force, indicated by the arrows P, to the septal tissues, as discussed above. The vertical direction is indicated by arrows V, and the horizontal direction is indicated by arrows H.

Once deployed, clip 18 is centered horizontally across the PFO because the movement of spaced, elongate connecting strands 36 and 38 is limited by the edges of the PFO tunnel. Thus, clip 18 consistently applies pressure to the overlapping layers of septal tissue at the locations where outwardly angled side strands 28 and 42 and 30 and 44 overlap. Lesser pressures are also applied at the locations where peaks 26 and 40 and loops 32, 34, 46, and 48 engage septum primum and septum secundum.

As illustrated, the angle of peak 26, i.e. the angle formed by wires 28 and 30, is slightly larger than 90 degrees. Of course, one skilled in the art will recognize that the "peak angle" could be 180°, which would effectively create a transverse strand across the tissues forming the PFO tunnel. The "peak angles" could be different on one side of the septum than on the other, e.g. the "peak angles" could vary on the closure members in the left and right atria. When determining the "peak angles" for a given clip according to the invention, one design consideration would be the difference in thickness between septum secundum and septum primum. The device should have a design that compresses (or at least holds) septum primum and septum secundum together.

Depending on the anatomy of the septum and the forces applied by the clip, the loops and peaks may contact the septum. Since the septum is generally stiff but not actually rigid, the tissue will generally conform to the forces applied to it. This is particularly true for septum primum. Accordingly, any illustration of the clip as shown schematically in the heart should be considered as exemplary and not limiting.

Figure 5A:
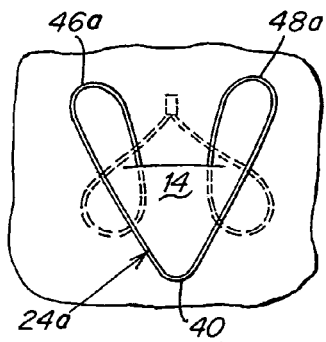
FIGS. 5a and 5b are front elevational views of a PFO closure clip according to a second embodiment of the present invention as seen from the left and right atria, respectively.
Figure 5B:
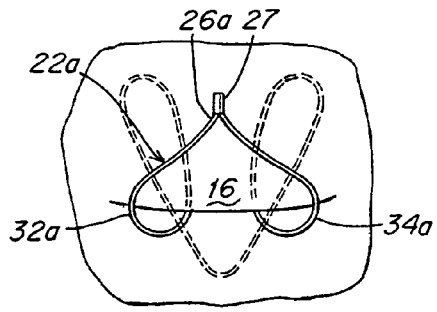

In at least some embodiments, the closure clip of the present invention is repositionable and/or retrievable. For example, as shown in FIG. 5, an attachment point 27 may be included on peak 26a of closure member 22a to facilitate manipulation of the clip device during and following its deployment. In the various embodiments described below, reference numerals which apply to a feature of the clip are used consistently and are given a letter identifier. For example, peak 26 is peak 26a in the embodiment described with reference to FIG. 5, 26b in the embodiment described with reference to FIG. 6, etc. In particular embodiments, the closure clip may be modified such that peak 26a and, correspondingly, point 27 are pointing downwards, as shown in FIGS. 6a, 6b, 7a, 7b, 8a, 8b and described below, so as to further facilitate manipulation and recovery of the clip device.

Figure 6A:
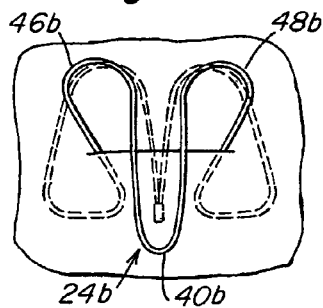
FIGS. 6a and 6b are front elevational views of a PFO closure clip according to a third embodiment of the present invention as seen from the left and right atria, respectively.
Figure 6B:
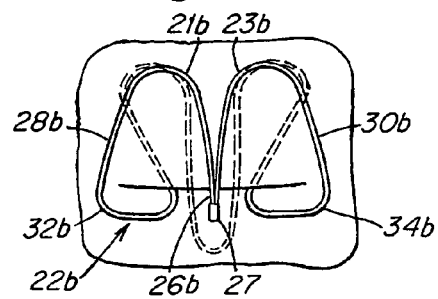

The closure clip of the present invention may have a variety of configurations. In one embodiment (FIGS. 6a and 6b), the clip is modified to concentrate the compressive force along the center of the PFO. As shown in FIG. 6a, loops 46b and 48b of second closure member 24b are folded inward such that strands 42b and 44b are straightened and elongated through the vertical center of closure member 24b, terminating in arcuate peak 40b. Additionally, as shown in FIG. 6b, spaced loops 21b and 23b may be formed opposite loops 32b and 34b in the uppermost extremities of strands 28b and 30b of first closure member 22b, such that peak 26b is forced downwards and elongated through the vertical center of closure member 22b. The elongated central peak 40b of closure member 24b and the elongated peak 26b of closure member 22b concentrate the compressive force at the center of the defect in the left and right atria, respectively. Applying pressure to the center of the defect, rather than its ends, is considered to produce a more effective closure. Further, as noted above, the downwardly-pointing peak 26b of closure member 22b in the right atrium facilitates manipulation and recovery of the clip following its deployment.

Figure 7A:
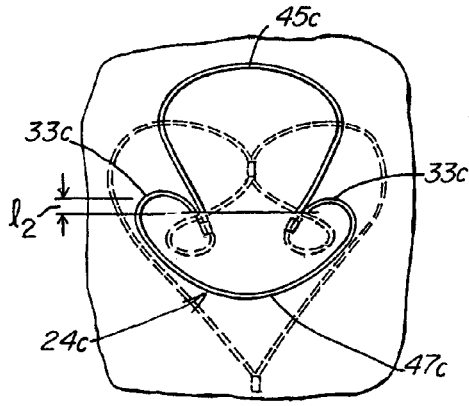
FIGS. 7a and 7b are front elevational views of a PFO closure clip according to a fourth embodiment of the present invention as seen from the left and right atria, respectively.
Figure 7B:
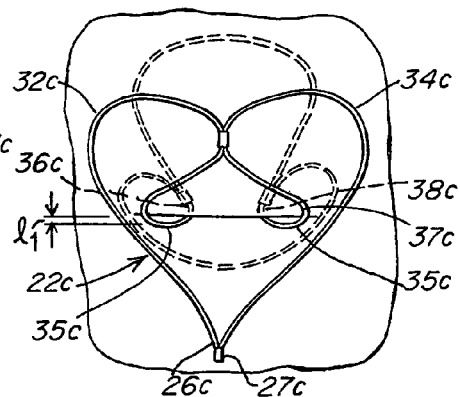

The clip 18c may also be modified to ensure it remains vertically centered after being deployed across the PFO (FIGS. 7a and 7b). "Vertically centered" refers to the portion of the device along the length of the PFO. It may be important to ensure that the device maintains a position along the length (longitudinal) of the PFO. In order to accomplish this using the structure of the device (instead of or in addition to a compressive force applied by the clip), the strands may be configured to limit the longitudinal motion of the device. In particular, as shown in FIG. 7a, the shape of second closure member 24c may be modified to form upper and lower loops 45c and 47c. As shown in FIG. 7b, closure member 22c may be inverted, and heart-shaped loop 37c may be included between loops 32c and 34c and connecting strands 36c and 38c. Looped ends 33c of lower loop 47c and looped ends 35c of heart-shaped loop 37c serve as vertical centering structures that act together to constrain the vertical movement of clip. The first vertical centering structures (i.e. looped ends 35c of heart-shaped loop 37c) and second vertical centering structures (i.e. looped ends 33c of lower loop 47c) are opposed across the overlapping layers of the septum. The movement of clip 18c is thereby limited in the left atrium to the height $l_2$ of end loops 33c and in the right atrium to the height $l_1$ of end loops 35c. Of course, other embodiments of the present invention may include the same type of vertical centering structures 33c or 35c in one or both closure members 22 and 24. Another advantage of the configuration of the clip device shown in FIGS. 7a and 7b is that there is better coverage on both sides of the defect and, as a result, better closure of the defect. Additionally, the configuration provides better dislodgement resistance since the device, once deployed, has limited movement in the longitudinal direction.

The connecting members also serve a horizontal centering function. Specifically, the connecting members may be designed to fit within the PFO tunnel such that there is little (or no) horizontal movement once the device is deployed. Horizontal centering is important because the dynamic conditions in the heart may tend to move the device. Of course, various configurations, including bent or slightly bent wires, to position the connecting members within the PFO tunnel are within the scope of this invention.

Figure 8A:
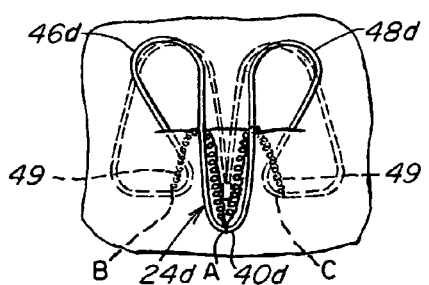
FIGS. 8a and 8b are front elevational views of a PFO closure clip according to a fifth embodiment of the present invention as seen from the left and right atria, respectively.
Figure 8B:
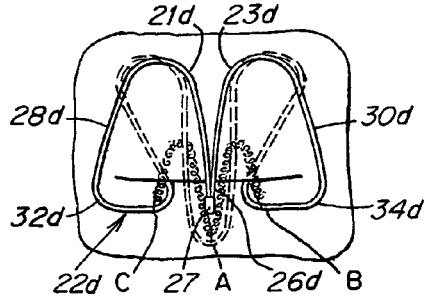

In a further embodiment, the movement of clip 18d across the defect is limited by small diameter centering elements 49, which may be of the type disclosed in U.S. Pat. No. 5,709,707, hereby incorporated by reference. The centering elements are attached to and connect closure members 22d and 24d. These centering elements may be springs and may be formed of metal, plastic, elastic materials, or shape memory materials (e.g. nitinol). The connectors are attached to closure members 22d and 24d such that the inherent tendency of the springs to straighten will center the clip 18d across the defect following its deployment. For example, as shown in FIGS. 8a and 8b, the springs may be positioned such that they connect point A of closure member 24d with points B and C of closure member 22d. The centering elements may be included in any of the embodiments of clip 18 or any of the embodiments of the invention described herein. The location of the centering elements may be varied according to the application. The centering elements are represented by coils in FIGS. 8a and 8b.

While closure members 22 and 24 of the various embodiments of clip 18 have been shown and described in pairs, the present invention is not limited to these illustrated combinations. In fact, a clip device including any of the various embodiments of closure member 22 disclosed herein in combination with any of the various embodiments of closure member 24 disclosed herein may be used to close a PFO and is considered within the scope of the present invention.

Figure 9:
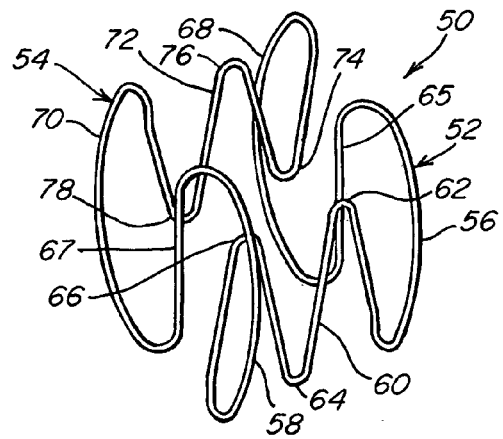
FIG. 9 is a perspective view of a PFO closure clip according to a sixth embodiment of the present invention.
Figure 10:
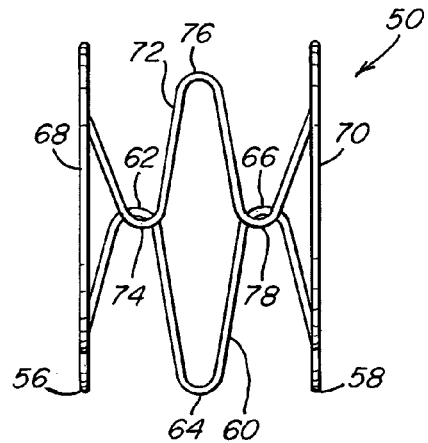
FIG. 10 is a front elevational view of the PFO closure clip of FIG. 9.

Referring now to FIGS. 9 and 10, another embodiment of a PFO closure clip according to the present invention, indicated generally at 50, is designed to provide a sufficient gripping force so that the clip maintains its position. The clip 50 includes a first substantially "S"-shaped section 52 and a second substantially "S"-shaped section 54. The first closure member of clip 50 includes a first C-shaped end 68 of the section 52 joined to a first C-shaped end 70 of the section 54 by a looped joiner strand 72 having three substantially "U"-shaped loops 74, 76, and 78. The second closure member of clip 50 includes a second C-shaped end 56 of the section 52 joined to a second C-shaped end 58 of the section 54 by a looped joiner strand 60 having three substantially "U"-shaped loops 62, 64, and 66. Loops 74, 76, and 78 are oriented in an opposed relationship to the loops 62, 64, and 66. It will be noted in FIG. 10 that the loops 62 and 66 are overlapped by the loops 74 and 78. Although FIGS. 9 and 10 depict a clip including a looped joiner strand having three U-shaped loops, the looped joiner strands of the clip devices according to the present invention may include one or more U-shaped loops. The first closure member is connected to the second closure member by connecting members attached to the closure members at their peripheries, i.e. ends 56 and 68 are connected by connecting strand 65 of section 52, while ends 58 and 70 are connected by connecting strand 67 of section 54. Connecting strands 65 and 67 are designed to extend through the inclined PFO tunnel 20 between septum primum and septum secundum.

Figure 11:
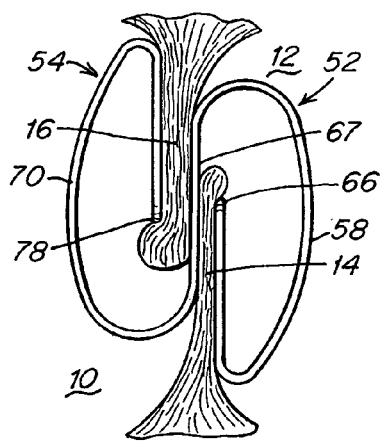
FIG. 11 is a side elevational view of the PFO closure clip of FIG. 9 disposed in a PFO.
Figure 12:
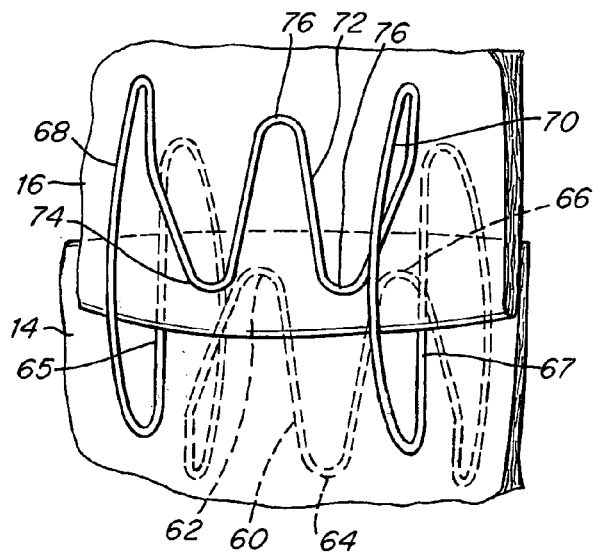
FIG. 12 is a perspective view of the PFO closure clip of FIG. 9 disposed in a PFO as seen from the right atrium.
Figure 13:
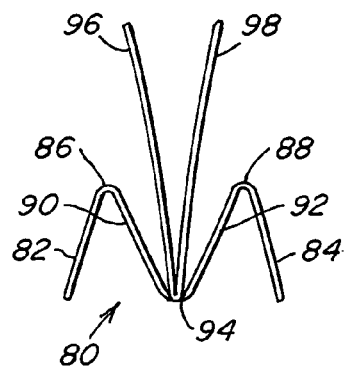
FIG. 13 is a front elevational view of a PFO closure clip according to a seventh embodiment of the present invention.

FIGS. 11 and 12 show the clip 50 in place to close a PFO. Clip 50 may be elongated and deployed through a catheter. The catheter enters the right atrium and is inserted through the PFO tunnel into the left atrium. The second closure member (i.e. ends 56 and 58 and joiner strand 60) is deployed into the left atrium, where it resumes the shape shown in FIG. 9. The catheter is then withdrawn through the PFO tunnel into the right atrium such that connecting strands 65 and 67 are deployed and extend through the PFO tunnel. Finally, the first closure member (i.e. ends 68 and 70 and joiner strand 72) is deployed into the right atrium, where it resumes the shape shown in FIG. 9. When so deployed, the first and second closure members apply a compressive force to the septal tissues, as shown in FIGS. 11 and 12. As shown in FIG. 12, loops 62, 64, and 66 of joiner strand 60 exert a compressive force against the surface of septum primum in the left atrium. Similarly, loops 74, 76, and 78 of joiner strand 72 exert a compressive force against the surface of septum secundum in the right atrium. These opposing forces urge the septal tissues together to close the defect.

Referring now to FIGS. 13-17, still another embodiment of the PFO closure clip of the present invention is provided. The clip 80 includes a first closure member having two, spaced prongs, e.g. spines, 96 and 98. Spines 96 and 98 are joined at their peripheries to angled sections 90 and 92, which are designed to extend through the PFO tunnel, by a first joinder 94. Angled sections 90 and 92 are connected by second joinders 86 and 88 to the periphery of the second closure member, which includes two spaced, downwardly extending prongs, e.g. arms, 82 and 84. While the clip 80 shown in FIG. 13 includes two spines in the first closure member, a greater number of spaced spines may be included by increasing the length of the first joinder 94 so as to space angled sections 90 and 92 and arms 82 and 84 further apart. As the number of spines in clip 80 is increased, the number of contact points between the clip device and the septal tissue is increased, thereby increasing the compressive force applied to septum primum and septum secundum and, in at least some embodiments, producing a more effective closure of the defect.

Figure 14:
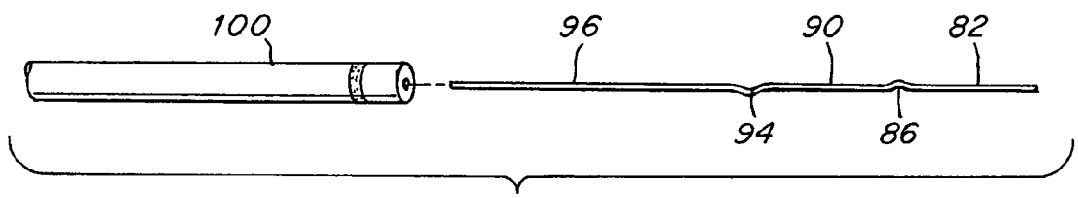
FIG. 14 is a side elevational view of the PFO closure clip of FIG. 13 straightened for insertion into a sheath.
Figure 15:
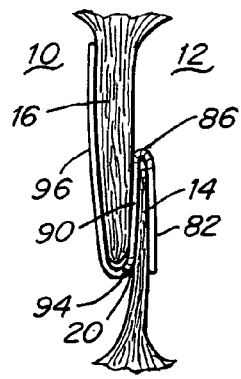
FIG. 15 is a side elevational view of the PFO closure clip of FIG. 13 in place in a PFO.

The clip 80 may be delivered through a catheter in a straight, elongate form. In at least some embodiments, the clip 80 is constructed from a shape memory material (e.g. nitinol), such that clip 80 resumes the shape shown in FIG. 13 following its deployment. Again, materials having thermal shape memory or superelasticity or both may be used. Thus, as shown in FIG. 14, clip 80 may be straightened and delivered through a catheter or sheath 100 with arms 82 and 84 positioned adjacent the forward end of the catheter 100. The catheter 100 is inserted into the left atrium through the PFO tunnel 20 between septum primum and septum secundum, and the second closure member (i.e. arms 82 and 84) is ejected up to the joinders 86 and 88. The arms 82 and 84 deploy downwardly into engagement with the surface of septum primum in the left atrium, and the catheter 100 is then drawn back through the PFO tunnel 20, deploying angled sections 90 and 92, which extend through the PFO tunnel. Finally, the first closure member is ejected from the catheter 100, and spines 96 and 98 engage the surface of septum secundum in the right atrium, as shown in FIG. 15. The arms 82 and 84 and spines 96 and 98 exert a compressive force upon septum primum and septum secundum, thereby closing the defect.

The clip 80 may be modified in various ways. Thus, according to some embodiments (FIGS. 16 and 17), the clip 80 is modified such that it engages a more extensive area of the septal tissue surrounding the PFO, thereby producing a more effective closure of defect. For example, in some embodiments, the clip 80 may be modified such that it engages septal tissue along the length of the defect. In one such embodiment, indicated generally at 102 in FIG. 16, the spines 96 and 98 of the first closure member are modified to include laterally extending bars 104 and 106 at their free upper ends. When clip 102 is deployed, bars 104 and 106 engage and apply force to a surface of septum secundum along the length of the defect in the right atrium. Another such embodiment, indicated generally at 110 in FIG. 17, includes a single spine 112 in the first closure member that extends upwardly from the second joinder 94 and terminates in a lateral crossbar 114. Lateral crossbar 114, like bars 104 and 106 of clip 102, engages a surface of septum secundum along the length of the defect in the right atrium. Additionally, a curved cross strut 116 may be included in the second closure member between arms 82 and 84 of clip 102 or 110. Cross strut 116 engages a surface of septum primum across the length of the defect in the left atrium, thereby increasing the compressive force applied to the defect by clip 102 or 110.

Figure 16:
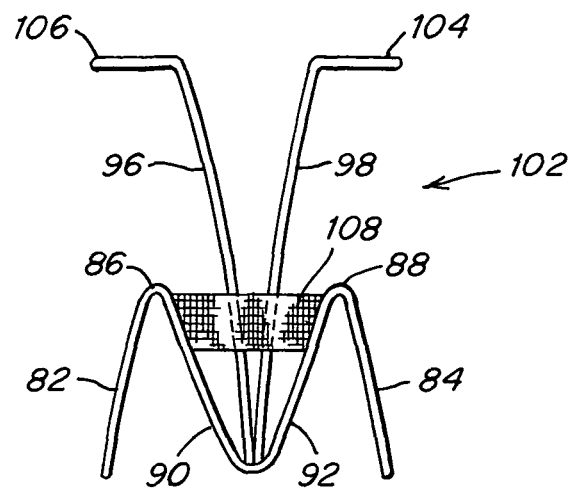
FIG. 16 is a front elevational view of an eighth embodiment of a PFO closure clip according to the present invention.
Figure 17:
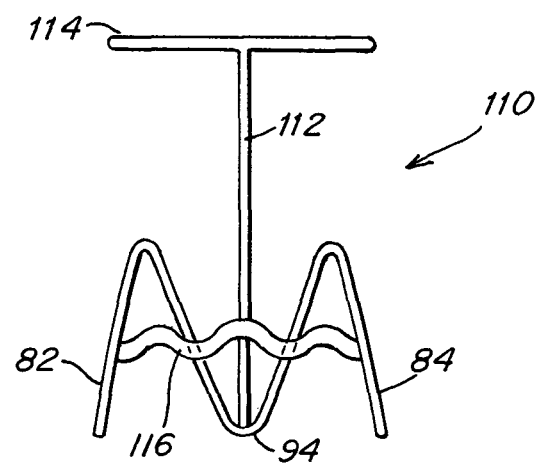
FIG. 17 is a front elevational view of a ninth embodiment of a PFO closure clip according to the present invention.

In still other embodiments, the clip 80 may be modified to encourage the anatomical closure of the overlapping layers of septal tissue by additional means. For example, as shown in FIG. 16, a flexible strip 108 formed of a material capable of promoting tissue growth may be attached between inclined sections 90 and 92 of clip 102. Strip 108 will unfurl when the clip is deployed and will be positioned in the PFO tunnel. Strip 108 may be formed of any flexible material capable of promoting tissue growth, including but not limited to polyester fabrics, Teflon-based materials, polyurethanes, other natural materials (e.g. collagen), or combinations of the foregoing materials. Although strip 108 is depicted as part of clip 102, it may be included in any of the various embodiments disclosed herein.

Any of the clip embodiments of the present invention may include a tissue scaffold on one or both closure members. The tissue scaffold promotes encapsulation and endothelialization, thereby further encouraging anatomical closure of septum primum and septum secundum. The tissue scaffold may be formed of any flexible material capable of promoting tissue growth, including but not limited to polyester fabrics, Teflon-based materials, polyurethanes, other natural materials (e.g. collagen), or combinations of the foregoing materials.

The compressive force applied by the closure members of any of the various embodiments described herein may be adjusted in a variety of ways. For example, the thickness of the strand or wire may be increased or decreased to adjust the compressive force. In general (and with other design considerations similar), a thicker strand or wire will provide higher compressive force. Additionally, various closure member configurations may be chosen to increase the compressive force. Generally, bends with smaller angles will provide more compressive force. One skilled in the art will recognize the various design modifications that could be used to adjust the compressive force of the device.

Having described embodiments of the present invention, it should be apparent that the invention is capable of other and different embodiments and may be modified in various respects, all without departing from the scope of the invention as defined by the appended claims. Accordingly, the foregoing drawings and description are to be regarded as illustrative in nature and not in a restrictive or limiting sense.

What is claimed is:

1. A device for closing a septal defect with two overlapping layers of septum primum and septum secundum dividing a left atrium and a right atrium in a mammalian heart, the device having a delivery configuration and a deployed configuration, the device comprising:

an elongated element arranged in a closed loop in both the delivery and deployed configurations, the elongated element defining a first and a second opposed closure member and at least two connecting members, the elongated element being elongated and straightened in the delivery configuration, the first and second opposed closure members disposed on opposite sides of the septum, each closure member having a periphery, wherein each of the first and second closure members includes two curved portions, the two curved portions of the first closure member being connected at a first peak at a vertical center of the first closure member, the two curved portions of the second closure member being connected at a second peak at a vertical center of the second closure member, wherein the first and second peak generally oppose one another on opposite sides of the septum in the deployed configuration, and the first closure member and the second closure member configured to apply a compressive force to the overlapping layers in the deployed configuration, and wherein the first and second opposed closure members are substantially parallel to each other in the deployed configuration, the at least two connecting members attached to each of said closure members at a location on the periphery of said closure members, wherein the connecting members extend between the overlapping layers of septum primum and septum secundum, and portions of the at least two connecting members and the two curved portions of each of the first and second opposed closure members disposed to provide a compressive force to the overlapping layers of septum primum and septum secundum, wherein, in the deployed configuration, the first and second closure members are substantially symmetric, the first closure member is directed generally in a first direction, and the second closure member is directed generally in a direction opposite to the first direction across a longitudinal axis transverse to the connecting members, and wherein, in the deployed configuration, the compressive force is applied to the overlapping layers at locations where portions of the elongated element overlap, and wherein in the deployed configuration, the compressive force is concentrated at the center of the septal defect along the vertical center of the first closure member and the vertical center of the second closure member.

2. The device of claim 1, wherein said first closure member is sized and shaped to apply a compressive force to the layers of septum primum and septum secundum in the right atrium and said second closure member is sized and shaped to apply a compressive force to the layers of septum primum and septum secundum in the left atrium.

3. The device of claim 1, wherein said device includes a material selected from the group consisting of metals, non-metallic materials, bioabsorbable polymers, spring steel, shape memory materials, bioabsorbable shape memory polymers, and combinations thereof.

4. The device of claim 3, wherein said device is constituted at least in part of nitinol.

5. The device of claim 1, wherein each of said first and second peaks are arcuate peaks.

6. The device of claim 5, wherein said arcuate peaks are oriented such that said arcuate peak of said first closure member is directed generally in a first direction and said arcuate peak of said second closure member is directed generally in an opposite direction.

7. The device of claim 6, said first closure member further comprising a point adapted to facilitate removal or repositioning of the device.

8. The device of claim 6, wherein the arcuate peak of the first closure member extends through the vertical center of the first closure member and the arcuate peak of the second closure member extends through the vertical center of the second closure member.

9. The device of claim 1, wherein the passage between septum primum and septum secundum forms a longitudinal axis and wherein said first and second closure members are configured to prevent movement along said longitudinal axis when said device is deployed.

10. The device of claim 9, wherein said first closure member contains first vertical centering structures and said second closure member contains second vertical centering structures such that, when said device is deployed, said first vertical centering structures are located in the right atrium, said second vertical centering structures are located in the left atrium, and said first and second vertical centering structures are opposed across the overlapping layers of septum primum and septum secundum.

11. The device of claim 10, wherein said first and second vertical centering structures include loops.

12. The device of claim 1, wherein said device further includes at least one centering element connecting said first and second closure members.

13. The device of claim 12, wherein said at least one centering element includes a material selected from the group consisting of metals, plastics, elastic materials, and shape memory materials.

14. The device of claim 13, wherein said at least one centering element is constituted at least in part of nitinol.

15. The device of claim 1, wherein each of said first and second closure members includes two C-shaped ends connected by a looped joinder strand including at least one U-shaped loop.

16. The device of claim 15, wherein said looped joinder strand of said first closure member is directed generally in a first direction and said looped joinder strand of said second closure member is directed generally in an opposite direction.

17. The device of claim 16, wherein each looped joinder strand includes three U-shaped loops.

18. The device of claim 16, wherein said looped joinder strand of said second closure member applies a compressive force to septum primum in the left atrium and said looped joinder strand of said first closure member applies a compressive force to septum secundum in the right atrium.

19. The device of claim 1, wherein at least one of said connecting members includes a generally straight section adapted to be disposed between septum primum and septum secundum.

20. The device of claim 19, wherein said at least one connecting member includes a curved section at the end of said connecting member.

21. The device of claim 20, wherein said closure member and said connecting member are formed of a single wire.

22. The device of claim 1, wherein the delivery configuration is of a generally low profile and is adapted to be delivered through a catheter.

23. A system for closing a septal defect with two overlapping layers of septum primum and septum secundum dividing a left atrium and a right atrium in a mammalian heart, the system comprising:

an elongated element defining a first and a second closure member and at least two connecting members, the at least two connecting members attached to each of said closure members at a location on the periphery of said closure members, said system having a first configuration adapted to be delivered through a catheter, said first configuration being of a generally low profile, the elongated element being arranged in a closed loop and being elongated and straightened in the first configuration, said system having a second configuration once delivered into the desired delivery site, the elongated element being arranged in a closed loop in the second configuration, the first and second opposed closure members disposed on opposite sides of the septum, each closure member having a periphery, wherein each of the first and second closure members includes two curved portions, the two curved portions of the first closure member being connected at a first peak at a vertical center of the first closure member, the two curved portions of the second closure member being connected at a second peak at a vertical center of the second closure member, wherein the first and second peak generally oppose one another on opposite sides of the septum in the second configuration, and the first closure member and the second closure member configured to apply a compressive force to the overlapping layers in the second configuration, and wherein the first and second opposed closure members are substantially parallel to each other in the second configuration, and wherein in said second configuration including said connecting members, the system is adapted to extend between the overlapping layers of septum primum and septum secundum such that portions of the at least two connecting members and the two curved portions of each of the first and second opposed closure members are disposed to provide a compressive force to the overlapping layers of septum primum and septum secundum, and wherein, in the second configuration, the compressive force is applied to the overlapping layers at locations where portions of the elongated element overlap, and wherein in the second configuration, the compressive force is concentrated at the center of the septal defect along the vertical center of the first closure member and the vertical center of the second closure member.

24. The system of claim 23, wherein said system further comprises a catheter through which said elongated element is adapted to be delivered when in said first configuration.

25. The system of claim 23, wherein, in said second configuration, said first closure member is sized and shaped to apply a compressive force to the layers of septum primum and septum secundum in the right atrium and said second closure member is sized and shaped to apply a compressive force to the layers of septum primum and septum secundum in the left atrium.

26. The system of claim 23, wherein said system includes a material selected from the group consisting of metals, nonmetallic materials, bioabsorbable polymers, spring steel, shape memory materials, bioabsorbable shape memory polymers, and combinations thereof.

27. The system of claim 26, wherein said system is constituted at least in part of nitinol.

28. The system of claim 23, wherein each of said first and second peaks are arcuate peaks.

29. The system of claim 28, wherein, in said second configuration, the arcuate peaks are oriented such that said arcuate peak of said first closure member is directed generally in a first direction and said arcuate peak of said second closure member is directed generally in an opposite direction.

30. The system of claim 28, wherein said first closure member further comprises a point adapted to facilitate removal or repositioning of the system.

31. The system of claim 23, wherein the passage between septum primum and septum secundum forms a longitudinal axis and, in said second configuration, said first and second closure members are configured to prevent movement along said longitudinal axis.

32. The system of claim 31, wherein, in said second configuration, said first closure member contains first vertical centering structures and said second closure member contains second vertical centering structures, such that when said system is deployed, said first vertical centering structures are located in the right atrium, said second vertical centering structures are located in the left atrium, and said first and second vertical centering structures are opposed across the overlapping layers of septum primum and septum secundum.

33. The system of claim 32, wherein, in said second configuration, said first and second vertical centering structures include loops.

34. The system of claim 23, wherein said system further includes at least one centering element connecting said first and second closure members.

35. The system of claim 34, wherein said at least one centering element includes a material selected from the group consisting of metals, plastics, elastic materials, and shape memory materials.

36. The system of claim 35, wherein said at least one centering element is constituted at least in part of nitinol.

37. The system of claim 23, wherein, in said second configuration, each of said first and second closure members of said system includes two C-shaped ends connected by a looped joinder strand including at least one U-shaped loop.

38. The system of claim 37, wherein, in said second configuration, said looped joinder strand of said first closure member is directed generally in a first direction and said looped joinder strand of said second closure member is directed generally in an opposite direction.

39. The system of claim 38, wherein, in said second configuration, said looped joinder strand includes three U-shaped loops.

40. The system of claim 38, wherein said looped joinder strand of said second closure member applies a compressive force to septum primum in the left atrium and said looped joinder strand of said first closure member applies a compressive force to septum secundum in the right atrium.

41. The system of claim 23, wherein, in the deployed configuration, the first and second closure members are substantially symmetric, the first closure member is directed generally in a first direction, and the second closure member is directed generally in a direction opposite to the first direction across a longitudinal axis transverse to the connecting members.

42. The system of claim 23, wherein said elongated element is formed of a single wire.

43. A system for closing a septal defect with two overlapping layers of tissue, the system having a delivery configuration and a deployed configuration, the system comprising:

an elongated element arranged in a closed loop in both the delivery and deployed configurations, the elongated element defining a first and a second closure members and at least two connecting members, the elongated element being elongated and straightened in the delivery configuration, the first and second opposed closure members disposed on opposite sides of the tissue, each closure member having a periphery, wherein each of the first and second closure members includes two curved portions, two elongate side strands, and a peak at a vertical center of the first and second closure members, the peak joining the two elongate side strands, and each peak having a peak angle of about 90 degrees or less, the first closure member and the second closure member configured to apply a compressive force to the overlapping layers in the deployed configuration, and wherein the first and second opposed closure members are substantially parallel to each other in the deployed configuration, the at least two connecting members attached to each of said closure members at a location on the periphery of said closure members, said connecting members attached to said closure members at an acute angle such that said closure members and said connecting members form a relatively flat device in the deployed configuration, wherein the connecting members extend between the overlapping layers of tissue, and portions of the at least two connecting members and the two curved portions of each of the first and second opposed closure members disposed to provide a compressive force to the overlapping layers, and wherein, in the deployed configuration, the compressive force is applied to the overlapping layers at locations where portions of the elongated element overlap, and wherein in the deployed configuration, the compressive force is concentrated at the center of the septal defect along the vertical center of the first and second closure members.

44. The system of claim 43, wherein said system further comprises a catheter through which said device is adapted to be delivered in an elongated form.

45. The system of claim 43, wherein said device includes a material selected from the group consisting of metals, non-metallic materials, bioabsorbable polymers, spring steel, shape memory materials, bioabsorbable shape memory polymers, and combinations thereof.

46. The system of claim 45, wherein said device is constituted at least in part of nitinol.

47. The system of claim 43, wherein each of said peaks of said first and second closure members of said device are arcuate peaks.

48. The system of claim 43, wherein said peaks are oriented such that said peak of said first closure member is directed generally in a first direction and said peak of said second closure member is directed generally in an opposite direction.

49. The system of claim 48, wherein said side strands joined to each peak are oriented from the peak to which the side strands are joined such that, when implanted, said side strands of each peak contact the tissue and apply a compressive force against the tissue.

50. The system of claim 48, wherein a defect defined by the two overlapping layers of tissue has a longitudinal axis and wherein each peak and said side strands joined to each corresponding peak are configured to extend transverse to the general direction of said longitudinal axis.

51. The system of claim 50, wherein said first closure member further comprises a point adapted to facilitate removal or repositioning of the device.

52. The system of claim 43, wherein the delivery configuration is of a generally low profile and is adapted to be delivered through a catheter.

* * * * *